United States Patent [19]

Suchsland et al.

[11] 4,307,037
[45] Dec. 22, 1981

[54] PROCESS FOR THE PRODUCTION OF IMINODIACETONITRILE

[75] Inventors: Helmut Suchsland, Rodenbach; Volker Häfner, Langenselbold; Axel Kleemann, Hanau, all of Fed. Rep. of Germany

[73] Assignee: Degussa Aktiengesellschaft, Frankfurt, Fed. Rep. of Germany

[21] Appl. No.: 198,262

[22] Filed: Oct. 17, 1980

[30] Foreign Application Priority Data

Oct. 20, 1979 [DE] Fed. Rep. of Germany ....... 2942437

[51] Int. Cl.$^3$ .................... C07C 120/00; C07C 121/43
[52] U.S. Cl. ................................................ 260/465.5 A
[58] Field of Search ................................ 260/465.5 A

[56] References Cited

U.S. PATENT DOCUMENTS

| 2,794,044 | 5/1957 | Miller | 260/465.5 A |
|---|---|---|---|
| 3,167,580 | 1/1965 | Saunders et al. | 260/465.5 A |
| 3,412,137 | 11/1968 | Stutts | 260/465.5 A |
| 3,886,198 | 5/1975 | Philbrook et al. | 260/465.5 A |
| 3,904,668 | 9/1975 | Gaudette et al. | 260/465.5 A |
| 3,988,360 | 10/1976 | Gaudette et al. | 260/465.5 A |
| 3,993,681 | 11/1976 | Cullen | 260/465.5 A |

FOREIGN PATENT DOCUMENTS 2613994 10/1976 Fed. Rep. of Germany .
2639874  3/1977 Fed. Rep. of Germany .

*Primary Examiner*—Joseph Paul Brust
*Attorney, Agent, or Firm*—Cushman, Darby & Cushman

[57] ABSTRACT

The invention is directed to a process for the production of iminodiacetonitrile by reaction of hexamethylenetetramine with hydrogen cyanide in acidic aqueous mediums. In this process the pH during the reaction which is 5.5 to 7.5 at the beginning is progressively lowered, altogether around 0.5 to 3.5 units and free formaldehyde is present only to a slight extent. Through this and in contrast to the known processes the formation of byproducts is suppressed and iminodiacetonitrile is produced directly in very good yields and sufficiently pure for further use.

14 Claims, No Drawings

PROCESS FOR THE PRODUCTION OF IMINODIACETONITRILE

BACKGROUND OF THE INVENTION

The invention is directed to a process for the production of iminodiacetonitrile by reaction of hexamethylenetetramine with hydrogen cyanide in acidic aqueous medium.

It is known that iminodiacetonitrile is formed by the action of hydrogen cyanide on ammonia and formaldehyde. The reaction is carried out in aqueous medium using 3 moles of hydrogen cyanide to 2 moles of ammonia and 3 moles of formaldehyde at pH values of 5.5 to 6.5 (Miller U.S. Pat. No. 2,794,044) or using 1.0 mole of hydrogen cyanide to 2.2 to 4.0 moles of ammonia and 0.6 to 1.0 mole of formaldehyde at pH values of 7 to 9 (Saunders U.S. Pat. No. 3,167,580).

It is also known to produce iminodiacetonitrile from hexamethylenetetramine and hydrogen cyanide in acidic aqueous medium. For this purpose in discontinuous operation, there are used per mole of hexamethylenetetramine 6 moles of hydrogen cyanide and the reaction is carried out at a temperature of 0° to 75° C. with addition of weak acids in a buffer mixture at a pH of 5.0 to 6.5 (Stutts, U.S. Pat. No. 3,412,137) or there is added per mole of hexamethylenetetramine at least 6 moles of hydrogen cyanide and the reaction takes place with the addition of strong acids at a temperature of 30° to 70° C., whereby the materials are partially mixed with each other in several steps, so in such manner that the pH in the reaction is held at 5.5 to 6.5 (Cullen, German OS No. 2,613,994) or there are used in continuous operation per mole of hexamethylenetetramine 5 to 7 moles of hydrogen cyanide, the reaction mixture is adjusted to a pH of 2.0 to 6.9 by means of strong acids and the reaction carried out in a reaction tube at 50° to 120° C. whereby in a given case portions of the acids are fed in at several places in the reaction tube (Philbrook U.S. Pat. No. 3,886,198).

Besides it is known to produce iminodiacetonitrile by reacting an aqueous mixture containing for every 1.0 mole of hexamethylenetetramine 1.8 to 2.2 moles of glycolonitrile with 5.2 to 6.6 moles of hydrogen cyanide at a pH of 4 to 10 and a temperature of 50° to 200° C. (Gaudette U.S. Pat. No. 3,904,668) or by reacting an aqueous mixture containing for every 1.0 moles of hexamethylenetetramine 1.0 to 2.2 moles of formaldehyde with 6.9 to 8.6 moles of hydrogen cyanide while adding acid at a pH of 5 to 10 and at a temperature of 50° to 250° C. (Gaudette, German OS No. 2,639,874).

A disadvantage in all of the known processes is that the iminodiacetonitrile produced contains to a considerable extent undesired byproducts such as glycolonitrile, nitrilotriacetonitrile and methylene bis iminodiacetonitrile. These byproducts either cannot be separated from the iminodiacetonitrile or in all events can be separated only with considerable difficulty and loss of yields. They are disturbing in the further use of the iminodiacetonitrile, for example in the hydrolysis to iminodiacetic acid or in the hydrogenation to diethylenetriamine or piperazine.

SUMMARY OF THE INVENTION

There has now been discovered a process for the production of iminodiacetonitrile by reaction of hexamethylenetetramine with hydrogen cyanide in aqueous acid medium which is characterized by carrying out the reaction at a temperature of about 30° to 90° C. and acid is added to the reaction mixture in such manner that the reaction is begun at a pH of about 5.5 to 7.5 and the pH is reduced during the reaction about 0.5 to 3.5 units.

With this process the iminodiacetonitrile is obtained in better yields than with the known processes. It is separated directly in outstanding purity from the reaction mixture and especially does not contain disturbing amounts of byproducts such as glycolonitrile, nitrilotriacetonitrile and methylene-bis-iminodiacetonitrile. Besides it is advantageous that the mother liquor can be repeatedly recycled and used as further starting material because byproducts are only formed in insignificant amounts.

In the process of the invention as starting material there is employed hexamethylenetetramine in aqueous medium. In so doing, preferably the concentration is so chosen that the hexamethylenetetramine is present completely dissolved. In place of hexamethylenetetramine there can also be used a corresponding mixture of formaldehyde and ammonia in water, insofar as this mixture is aged to such an extent that predominantly there is present hexamethylenetetramine. The hydrogen cyanide can be employed in any form, for example, as gas, liquid or in aqueous solution.

The molar ratio of hexamethylenetetramine to hydrogen cyanide can be selected in a wide range. Generally, it is suitable per mole of hexamethylene to use at least about 6 moles of hydrogen cyanide, although the process can also be operated with lesser amounts of hydrogen cyanide. In most cases, it is advantageous not to use more than about 10 moles, especially not more than 8 moles of hydrogen cyanide per mole of hexamethylenetetramine. Preferably there are employed 6 moles of hydrogen cyanide per mole of hexamethylenetetramine.

The reaction is suitably carried out at a temperature of 30° to 90° C. Preferably the temperature is 40° to 70° C., especially a temperature of 50° to 60° C.

According to the invention the reaction takes place with reducing pH during the reaction. Acid is added to change the pH. There can be used any acid which is suited for the desired change in pH. These types of acid are for example, organic acids such as acetic acid, propionic acid, oxalic acid and lactic acid or inorganic acids such as the hydrohalic acids, e.g., hydrochloric acid or hydrobromic acid, perchloric acid and phosphoric acid. Preferably sulfuric acid is used.

At which pH the reaction is begun and at which pH it is ended depends in a given case to a certain extent on the molar ratio of hexamethylenetetramine to hydrogen cyanide, the type of acid used to regulate the pH and the reaction temperature. Generally, the reaction mixture at the beginning has a pH of about 5.5 to 7.5, preferably 5.5 to 7.0. This pH during the reaction, with advantage continuously or intermittently progressively, is reduced about 0.5 to 3.5, preferably about 1.0 to 2.5, units, so that the reaction mixture at the end of the reaction in general has a pH of at most about 5.0, preferably from 4.0 to 5.0.

The addition of acid takes place continuously or intermittently, suitably in such manner that the concentration of free formaldehyde based on the total reaction mixture does not exceed about 3 weight percent. Preferably, the concentration of free formaldehyde is 0.1 to 1.5 weight percent, especially 0.5 to 1.0 weight percent.

It is generally advantageous that the reaction mixture at the end of the reaction contains at least enough water that the iminodiacetonitrile formed is present in completely dissolved form. The necessary amounts of water are suitably introduced with the starting materials, the hexamethylenetetramine and the hydrogen cyanide as well as the acid. The iminodiacetonitrile formed is obtained from the reaction mixture in known manner, for example by crystallization in cooling the reaction mixture.

Unless otherwise indicated all parts and percentages are by weight.

The process can comprise, consist essentially of or consist of the steps set forth and the materials employed can comprise, consist essentially of or consist of those set forth.

DETAILED DESCRIPTION

Example 1

There was present a solution of 140.2 grams (1 mole) of hexamethylenetetramine in 600 ml of water. This solution was mixed with 162.2 grams (6 moles) of liquid hydrogen cyanide. The mixture was adjusted at room temperature to a pH of 6.5 by the addition of concentrated sulfuric acid and then heated to 45° C. By further addition of the acid the pH was lowered to 6.2. In so doing, the temperature increased to 60° C. While the temperature was further held to 55° to 60° C., the pH was lowered in the course of 40 minutes to 5.0, while concentrated sulfuric acid was added in a uniform stream. The content of free formaldehyde hereby was 0.7 to 0.9%. Altogether, there was used 0.63 mole of sulfuric acid. The reaction mixture was then held for a further 15 minutes at 40° to 50° C. and subsequently cooled to 5° C. The iminodiacetonitrile, while crystallized out during this was filtered off, washed with 20 ml of ice cold water and dried under reduced pressure. The product had a melting point of 77° to 78° C. According to gas chromatographic and thin layer chromatographic examination it consisted of 99.5% iminodiacetonitrile and of 0.5% methylene-bis-iminodiacetonitrile. The yield of iminodiacetonitrile was 259 grams, corresponding to 90% based on the hexamethylenetetramine employed as well as on the hydrogen cyanide employed.

Example 2

(a) There was present the 510 ml of mother liquor which remained after filtering off the iminodiacetonitrile produced and crystallized out according to Example 1. After the addition of 90 ml of water there were dissolved in this mother liquor 140.2 grams (1 mole) of hexamethylenetetramine. Then there were added 162.2 grams (6 moles) of hydrogen cyanide. Otherwise the process was as in Example 1. The product obtained consisted of 99.7% iminodiacetonitrile and 0.3% methylene-bis-iminodiacetonitrile. The yield of iminodiacetonitrile amounted to 276 grams, corresponding to 96%.

(b) The procedure was as in (a) but there was present the mother liquor from (a). The product obtained consisted of 93.7% iminodiacetonitrile, 0.3% methylene-bis-iminodiacetonitrile and 6.0% ammonium sulfate. The yield of iminodiacetonitrile amounted to 97%.

(c) The procedure was as in (a) but there was present the mother liquor from (b). The product contained 7.0% ammonium sulfate. The yield of iminodiacetonitrile amounted to 97%.

Example 3

The procedure was according to Example 2(c) but there was only reused a portion of 250 ml of the mother liquor from Example 2(b). To this 350 ml water, 1 mole hexamethylenetetramine and 6 moles of hydrogen cyanide were added. For the rest the process of Example 1 was followed. The product had a melting point of 77° to 78° C. The iminodiacetonitrile contained no detectable impurities. The yield was 96%.

Example 4

The procedure was as in Example 1 but instead of sulfuric acid there was used 37 percent hydrochloric acid. The yield of iminodiacetonitrile was 83%. The product was 99.0 percent pure. It contained 1.0% methylene-bis-iminodiacetonitrile as impurity. For a further charge there was used the mother liquor remaining after the separation of the iminodiacetonitrile. To this there were added 1 mole of hexamethylenetetramine and 6 moles of hydrogen cyanide. Otherwise, the process was as in Example 1 but there was used as acid 37% hydrochloric acid. The yield was 91%. The product was 99.0% pure. It contained 1.0% of methylene-bis-iminodiacetonitrile as impurity.

Example 5

The procedure as in Example 1 but instead of sulfuric acid there was used 85 percent phosphoric acid. The yield of iminodiacetonitrile was 91%. The product was 99.2% pure. It contained 0.8% methylene-bis-iminodiacetonitrile as impurity. For a further charge there was used the mother liquor remaining after the separation of the iminodiacetonitrile. There was added to this 1 mole of hexamethylenetetramine and 6 moles of hydrogen cyanide. Otherwise the procedure was as in Example 1 but there was used as acid 85 percent phosphoric acid. The yield was 97%. The product was 99.5 percent pure. It contained 0.5% methylene-bis-iminodiacetonitrile as impurity.

Example 6

The procedure was as in Example 1 but in place of sulfuric acid there was used acetic acid. The yield of iminodiacetonitrile was 90%. No impurities were detectable in the product. For a further charge there was used the mother liquor remaining after the separation of the iminodiacetonotrile. To this there were added 1 mole of hexamethylenetetramine and 6 moles of hydrogen cyanide. Otherwise the procedure was as in Example 1 but there was used as the acid, acetic acid. The yield was 96%. No impurities were detectable in the product.

Example 7

The procedure was as in Example 1 but in place of sulfuric acid there was used 90% lactic acid. The yield of iminodiacetonitrile was 92%. No impurities were detectable in the product. For a further charge there was used the mother liquor remaining after the separation of the iminodiacetonitrile. To this there were added 1 mole of hexamethylenetetramine and 6 moles of hydrogen cyanide. Otherwise the procedure was as in Example 1 but there was used as the acid, 90% lactic acid. The yield was 96%. No impurities were detectable in the product.

Example 8

The procedure was as in Example 1 but there was present a solution of 140.2 grams (1 mole) of hexamethylenetetramine in 327 grams of water. The yield was 93%. The product was 99.2 percent pure. It contained 0.8% of methylene-bis-iminodiacetonitrile as an impurity.

Example 9

The procedure was as in Example 1 but there was present a solution of 140.2 grams (1 mole) of hexamethylenetetramine in 327 grams of water. As acid there was used 37 percent hydrochloric acid. The yield was 85%. The product was 99 percent pure. It contained 1.0% of methylene-bis-iminodiacetonitrile as an impurity.

Example 10

The procedure was as in Example 1 but there was present a solution of 140.2 grams (1 mole) of hexamethylenetetramine in 327 grams of water. As acid there was used 85 percent phosphoric acid. The yield was 93%. The product was 99.2 percent pure. It contained 0.8% of methylene-bis-iminodiacetonitrile as an impurity.

Example 11

The procedure was as in Example 1 but there was present a solution of 140.2 grams (1 mole) of hexamethylenetetramine in 327 grams of water. As acid there was used acetic acid. The yield was 91%. The product was 99.5 percent pure. It contained 0.5% of methylene-bis-iminodiacetonitrile as an impurity.

Example 12

The procedure was as in Example 1 but there was present a solution of 140.2 grams (1 mole) of hexamethylenetetramine in 327 grams of water. As acid there was used 90 percent lactic acid. The yield was 94%. No impurities were detectable in the product.

Example 13

The procedure was as in Example 1 but the pH at beginning of the reaction was 6.0. By the addition of 0.65 mole of sulfuric acid the pH was lowered to 5.2. The yield of iminodiacetonitrile was 88%. The product was free from nitrilotriacetonitrile but contained 1.5% of methylene-bis-iminodiacetonitrile.

Example 14

The reaction was carried out in 5 loop reactors, each having a spatial content of 182 ml. The reactors were connected in series and the reaction mixture was flowed through them in succession. The reaction temperature in the first reactor was 50° C. and in the subsequent reactors 56° to 60° C. In each reactor separate from each other there was fed in sulfuric acid. Through this the pH was held in the first reactor at 6.2, in the second reactor 6.0, in the third reactor 5.8, in the fourth reactor 5.6 and in the fifth reactor 5.4. In all of the reactors, the content of free formaldehyde was between 0.6 and 1.0%. There was supplied to the first reactor in homogeneous flow hourly 910 ml of a starting mixture which contained 1 mole of hexamethylenetetramine, 6 moles of hydrogen cyanide and 600 ml of water and had a pH of 6.5. The reaction mixture which came out of the fifth reactor was treated hourly with 2.5 grams of activated carbon, filtered at 50° to 55° C. and then cooled to crystallize out the iminodiacetonitrile. 30% of the mother liquor which remained after the separation of the iminodiacetonitrile was discarded. The rest of the mother liquor was returned and used for the preparation of starting mixtures of a corresponding composition. At the stationary ratios which were established after repeated recycling of the mother liquor, the starting mixture contained 1 mole of hexamethylenetetramine, 6 moles of hydrogen cyanide and 335 ml of water. There resulted then an hourly yield of 278 grams, corresponding to 97%, based on the hexamethylenetetramine employed as well as on the hydrogen cyanide employed. The product was colorless. It was 99.5 percent pure and contained 0.5% of methylene-bis-iminodiacetonitrile as impurity.

What is claimed is:

1. A process for the production of iminodiacetonitrile comprising reacting hexamethylenetetramine with hydrogen cyanide in aqueous acidic medium at 30° to 90° C. and adding acid in such manner to the reaction mixture that the reaction begins at pH of about 5.5 to 7.5 and is reduced during the reaction by about 0.5 to 3.5 units and also so controlling the addition of the acid that the concentration of free formaldehyde present does not exceed about 3 weight percent.

2. A process according to claim 1 wherein the pH is reduced about 1.0 to 2.5 units.

3. A process according to claim 2 wherein for each mole of hexamethylenetetramine there is employed 6 moles of hydrogen cyanide.

4. A process according to claim 1 wherein for each mole of hexamethylenetetramine there is employed 6 moles of hydrogen cyanide.

5. A process according to claim 2 wherein for each mole of hexamethylenetetramine there is used at least about 6 moles of hydrogen cyanide.

6. A process according to claim 5 wherein there are used for each mole of hexamethylenetetramine about 6 to 10 moles of hydrogen cyanide.

7. A process according to claim 6 wherein there are used for each mole of hexamethylenetetramine about 6 to 8 moles of hydrogen cyanide.

8. A process according to claim 7 wherein the temperature is 40° to 70° C.

9. A process according to claim 8 wherein the temperature is 50° to 60° C.

10. A process according to claim 7 wherein the pH at the beginning of the reaction is 5.5 to 7.0.

11. A process according to claim 7 wherein the pH at the end of the reaction is not over about 5.0.

12. The process of claim 11 wherein the pH at the end of the reaction is 4.0 to 5.0.

13. The process of claim 12 wherein the concentration of free formaldehyde is 0.1 to 1.5%.

14. The process of claim 13 wherein the concentration of free formaldehyde is 0.5 to 1.0%.

* * * * *